United States Patent [19]

Straus

[11] Patent Number: 4,759,746

[45] Date of Patent: Jul. 26, 1988

[54] RETRO-BULBAR NEEDLE

[76] Inventor: Jeffrey G. Straus, 2300 Edenborn Ave., Apt. 350, Bldg. II, Metairie, La. 70001

[21] Appl. No.: 50,204

[22] Filed: May 14, 1987

[51] Int. Cl.$^4$ ............................................. A61M 31/00
[52] U.S. Cl. ....................................... 604/51; 604/272
[58] Field of Search .................. 604/51, 272, 273, 274

[56] References Cited

U.S. PATENT DOCUMENTS

| 762,603 | 6/1904 | Witkowski . | |
|---|---|---|---|
| 1,384,355 | 7/1921 | Smith . | |
| 1,503,399 | 7/1924 | Webb . | |
| 3,097,647 | 7/1963 | Roehr | 604/272 |
| 4,013,080 | 3/1977 | Froning | 128/347 |
| 4,200,096 | 4/1980 | Charvin | 604/272 |
| 4,496,353 | 1/1985 | Overland et al. | 604/272 |
| 4,511,356 | 4/1985 | Froning et al. | 604/164 |
| 4,518,383 | 5/1985 | Evans | 604/51 |

FOREIGN PATENT DOCUMENTS 1168224  7/1985  U.S.S.R. ............................ 604/272

OTHER PUBLICATIONS

American Journal of Ophthalmology, Jan. 1961–"The Development of Ophthalmic Anesthesia", by Walter S. Atkinson, M.D.

Primary Examiner—John D. Yasko
Attorney, Agent, or Firm—Collard, Roe & Galgano

[57] ABSTRACT

A needle for use in the administration of retro-bulbar or peri-bulbar anesthetics and a method for its use is set forth. The needle is composed of a hub portion having a central longitudinal axis therethrough, and a generally curved needle portion extending from the hub portion. The curved needle portion is made up of a first section extending generally outwardly away from the longitudinal axis of the hub, and a second section extending generally inwardly towards the longitudinal axis of the hub. The terminal section of the curved needle portion is oriented at a predetermined angle with respect to the longitudinal axis, which angle is normally about 30°. The needle also includes a vane which is oriented in the same plane as the terminal section so that the orientation of the end of the needle may be determined after insertion.

10 Claims, 3 Drawing Sheets

RETRO-BULBAR NEEDLE

BACKGROUND OF THE INVENTION

1. Field of the Invention

This invention relates to an instrument and method for administering retro-bulbar (or peri-bulbar) anesthetics. More specifically, a curved needle is disclosed which minimizes the attendant risk of such injection, commonly utilized in ocular surgery, such as cataract extraction, glaucoma filtering procedures, penetrating keratoplasty, repair of retinal detachment, and laser photocoagulation.

2. Description of the Prior Art

Needles used to date for retro-bulbar anesthetics have all been straight, of various lengths (the most popular currently approximately 38–50 mm), and calibers (most commonly 23 or 25 gauge). These needles have either been reusable or of the disposable type with pointed or rounded (Atkinson) tips.

The needle of the present invention differs from the needles which have been previously used to administer retro-bulbar anesthetics in that the needle of the present invention has a straight terminal section while the rest of the needle is curved.

While the prior art shows needles which are either angled with respect to the horizontal or are in some cases curved, none of these needles are suited for administering retro-bulbar or peri-bulbar anesthetics.

U.S. Pat. Nos. 4,013,080 and 4,511,356 to Froning et al disclose a needle having a curved terminal section for use in puncturing lumbar discs. Froning et al also discloses a vane for orienting the needle.

U.S. Pat. Nos. 762,603 to Witkowski and 4,518,383 to Evans disclose hypodermic needles which are angled from the central axis of the syringe.

U.S. Pat. Nos. 1,384,355 to Smith and 1,503,399 to Webb disclose hypodermic needles having some portion curved from the central axis of the hypodermic syringe.

While the prior art needles are similar in some respects to the hypodermic needle of the present invention, none of the patents cited disclose a needle suitable for use in administering retro-bulbar or peri-bulbar anesthetics, and none of these patents teach any method for such administration.

The present method of administering ophthalmic anesthesia is disclosed in the American Journal of Ophthalmology, Vol. 51, No. 1, January 1961, in an article by Walter S. Atkinson, M.D., entitled "The Development of Ophthalmic Anesthesia". The prior method, as described in the article, requires the insertion of the needle in the infero-temporal quadrant of the orbit with the needle being directed straight back well away from the eyeball until the point is beyond the globe. It is then pointed superiorly towards the apex of the orbit and inserted to a depth of 2.5–3.5 cm, and the injection is then made in the muscle cone.

The design of the present invention is advantageous in decreasing many of the risks of the common complications of the now utilized method of retro-bulbar injection.

One common complication is retro-bulbar hemorrhage which is reduced with the use of the needle of the present invention because less orbital space is violated. The straight needle of the prior art is passed posteriorly until the tip is posterior to the equator of the globe, and it is then angled superiorly as it is passed further posteriorly towards the apex of the orbit. Thus, a quasi-triangular planar space is violated by the needle. With the curved needle of the present invention, only a basically curvilinear space is violated with consequently less disruption of intra-orbital tissues and therefore vessels.

With the use of the needle of the present invention, there is less stress on the violated tissue. The tissue penetrated by the straight needle is stretched as the needle is lifted for passage in an increasingly superior direction. The shaft of the needle also may displace the globe superiorly as the tip is directed towards the apex, and this further adds to the tension placed on the intra-orbital vessels, thereby rendering them more susceptible to rupture. The curved needle does not "tent" or stretch the penetrated tissue, nor does it displace the globe in order to gain access to the muscle cone behind it. The curved needle passes around the globe.

Another advantage of the needle of the present invention is that there is increased distance from the central retinal artery and vein when the needle is inserted. The central retinal artery and vein approach the optic nerve infero-medially. The curved needle introduced infero-temporally passes more temporal than does the straight needle and, consequently, is further from the retinal artery and vein.

Furthermore, use of the needle and method of the present invention, reduces the possibility of injury to the optic nerve. The angulation of the straight terminal section of the needle of the present invention approximates the angle at which the optic nerve travels in the axial plane between the globe and the optic foramen. The approach of the needle tip is consequently more parallel to the optic nerve than is the straight needle used in the prior art which passes at a steeper angle superiorly than does the optic nerve.

In addition, the use of a needle with an arc of curvature greater than the arc of curvature of the eye renders penetration of the globe highly unlikely, given close attention to the technique of insertion.

The use of the needle of the present invention reduces the chance of the oculo-cardiac reflex. This "vaso-vagal reaction" is less likely to occur as a result of the decreased risks of retro-bulbar hemorrhage and the decreased tension upon the pre-paralyzed extra-ocular muscles by the displacement of the globe, as may occur to a small degree with conventional straight needles.

SUMMARY OF THE INVENTION

It is an object of this invention to provide a needle for use in the administration of retro-bulbar or peri-bulbar anesthetics.

It is still a further object of this invention to provide a needle and a method for its use which helps minimize the attendant risk of such injections which are commonly utilized in ocular surgery.

It is yet another object of this invention to provide a curved needle which violates less orbital space as the needle is passed posteriorly with respect to the globe.

It is yet an additional object of the invention to provide a curved needle which puts less stress on the tissue around the eye globe and does not displace the globe in order to gain access to the muscle cone behind it.

It is still a further object of the invention to provide a needle which is so shaped to pass further from the central retinal artery and the optic nerve than would be with the use of a straight hypodermic needle.

It is still an additional object of the invention to provide a needle shaped with an arc of curvature greater than the arc of curvature of the eye therefore rendering penetration of the globe unlikely.

It is yet another object of the invention to provide a needle wherein lack of contact of the shaft of the needle with the globe, as often occurs with a straight needle, decreases the resistance to passage which renders the resistance of penetration of the orbital septum, and consequently, the inter-muscular septum, more obvious and thereby increases assurance of having the needle tip within the muscle cone.

In accordance with the present invention, there is provided a needle for use in the administration of retro-bulbar or peri-bulbar anesthetics. The needle is composed of a hub portion having a central longitudinal axis therethrough and a generally curved needle portion extending from the hub portion. The curved needle portion is made up of a first section extending generally outwardly away from the longitudinal axis of the hub, and a second section extending generally inwardly towards the longitudinal axis.

The terminal section of the curved needle portion is oriented at a predetermined angle with the longitudinal axis, which angle is normally about 30°. The needle also includes a vane which is oriented in the same plane as the terminal section so that the orientation of the end of the needle may be determined after insertion.

Other objects and features of the present invention will become apparent from the following detailed description considered in connection with the accompanying drawings, which disclose several embodiments of the invention. It is to be understood that the drawings are to be used for the purpose of illustration only, and not as a definition of the limits of the invention.

BRIEF DESCRIPTION OF THE DRAWINGS

In the drawings, wherein similar reference characters denote similar elements throughout the several views.

DETAILED DESCRIPTION OF THE PREFERRED EMBODIMENT

Figure 1:
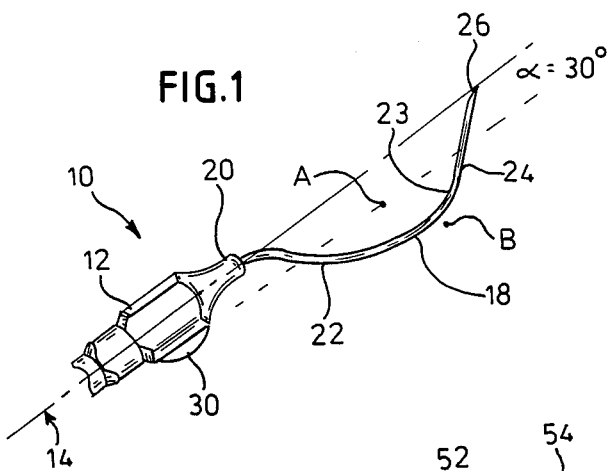
FIG. 1 is an isometric view of the needle of the present invention.
Figure 3:
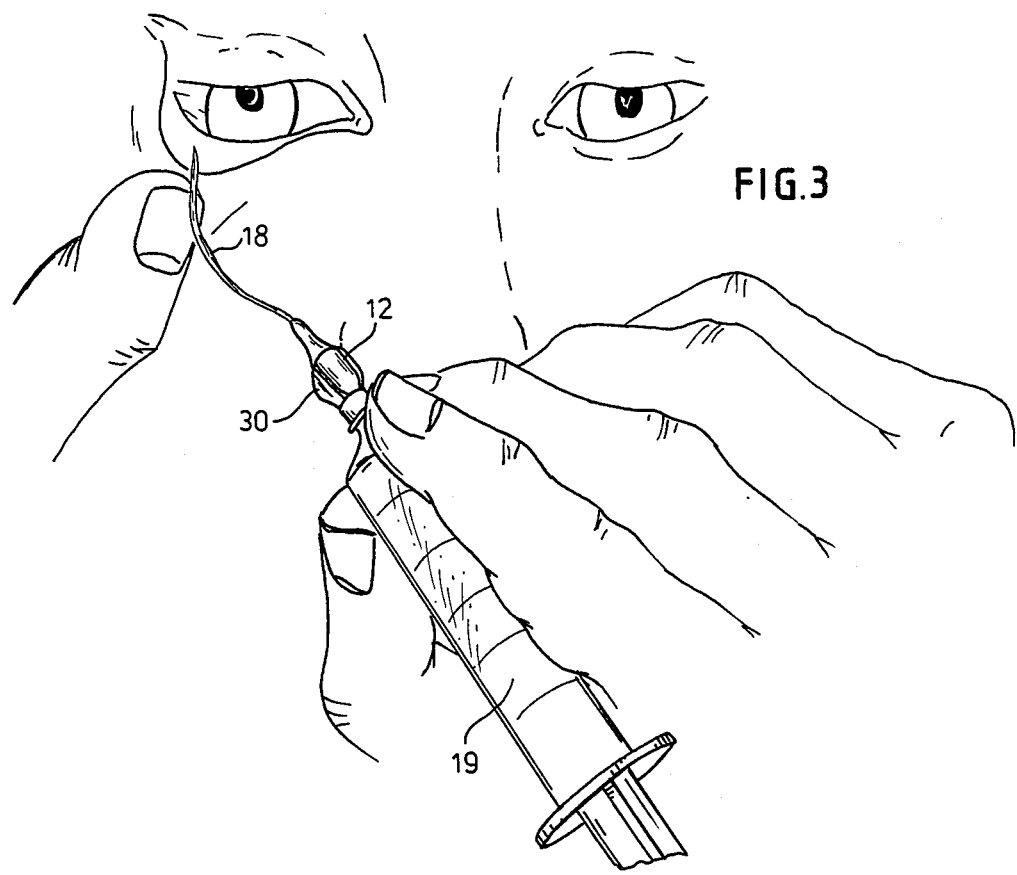
FIG. 3 is an isometric view from the surgeon's viewpoint showing the needle of the present invention just prior to insertion.

A retro-bulbar needle generally denoted as 10 is shown in FIG. 1. In the preferred embodiment, the needle 10 has a hub portion 12 which is designed to mate with standard hypodermic syringes 19 such as shown in FIGS. 3A, 4A, and 5A. The hub 12 has a longitudinal axis 14 running centrally therethrough.

The hub 12 has a central passageway 16 therethrough which is coaxial with the longitudinal axis 14. A generally curved needle portion 18 extends from a forward end 20 of the hub portion 12.

In the preferred embodiment, the generally curved needle 18 is composed of a first section 22 which extends generally outwardly away from the longitudinal axis 14 of the hub 12. The needle 18 has a second section 23 which extends generally inwardly towards the longitudinal axis 14. The needle portion 23 also has a terminal section 24 which is oriented at a predetermined angle to the longitudinal axis 14. In the preferred embodiment, this angle $\alpha$, as shown in FIG. 1, is between 25° and 35° in an attempt to parallel the approximate but variable angle of the intra-orbital optic nerve.

In the preferred embodiment, as seen in FIG. 1, the terminal section 24 is straight and not generally curved as are the first and second sections. At the end of the terminal section 24, there is a bevelled tip 26. In a preferred embodiment, the bevel of tip 26 is towards the concave aspect of the curved needle portion.

In the preferred embodiment, there is a vane 30 which is fixedly attached to the hub 12 and is located on the same plane as the needle portion 18. The preferred vane 30 is curved so that there are no sharp edges to contact the eye.

In the preferred embodiment, the entire needle portion 18, while curved with respect to the longitudinal axis 14, is in a single plane. The vane 30 would then be coplanar with the shaft of the needle 18 such that the curvature of vane 30 is in the same direction as the curvature of the needle portion 18 and consequently would provide an indication to the position of the orientation of the tip 26 and the needle portion 18.

The preferred needle portion 18 of the present invention is approximately 38–50 mm long, and is of a caliber of 23 or 25 gauge. The needle 10 may either be reusable or disposable with either a pointed or a rounded (Atkinson) tip (see FIG. 6). It is well known that any hypodermic needle could be made in any multiple combination of the above lengths and diameters.

In the preferred embodiment, the terminal section 24 is straight for approximately 10–12 mm.

In the preferred embodiment, from the hub 12 to the beginning of the terminal straight section 24, the needle portion 18 is curved and can be made available in various arcs of curvature. The particular arc most appropriate for each case could be determined, based upon the axial length of the eye, a measurement easily and routinely discerned by A-scan ultrasound during preoperative intra-ocular lens implant power calculations. Alternatively, an arc large enough to accommodate the overwhelming majority of eyes, e.g., up to 30 mm axial length, could be used as a standard.

In the preferred embodiment, the bevel on tip 26 is placed on the concave aspect A of the needle which would be towards the sclera of the eye, thereby decreasing the risk of penetration of the globe.

Each needle 10 can be used for either the right eye or the left eye, and can be used in a trans-conjunctival or trans-palpebral approach.

The preferred method for use of the needle 10 of the present invention is to first administer a local anesthetic mixture, such as 15 cc of 0.75% bupivacaine, 5 cc of 4% lidocaine HCl and 1 cc of hyaluronidase. The appropriate volume is injected through the appropriate needle to block the seventh cranial nerve on the side of the eye to be operated on. This local anesthetic administration does not utilize the needle of the present invention, but is well known in the medical art. As is also well known, this administration of local anesthesia can be accomplished with or without intravenous premedication with diazepam, midazolam, methohexital sodium, or inhaled premedication with an agent such as nitrous oxide.

In addition, one drop of topical ophthalmic anesthetic, such as 0.5% proparacaine HCl and one drop of topical ophthalmic antibiotic is instilled into the eye. Again, the administration of these medications is well known in the ophthalmic art.

The curved retro-bulbar needle 10 is then placed on a syringe 19 in such a way as to orient the gradations of the syringe facing toward the physician when the syringe 19 is held as it will be when passing the needle portion 18 intra-orbitally.

In the preferred method of administering the retrobulbar anesthesia, the patient is asked to maintain a gaze approximating the so-called "primary" position (this is normally staring straight ahead), although some physicians may prefer to have their patients assume the more conventional gaze of "up and in" or even "down and out".

Figure 4:
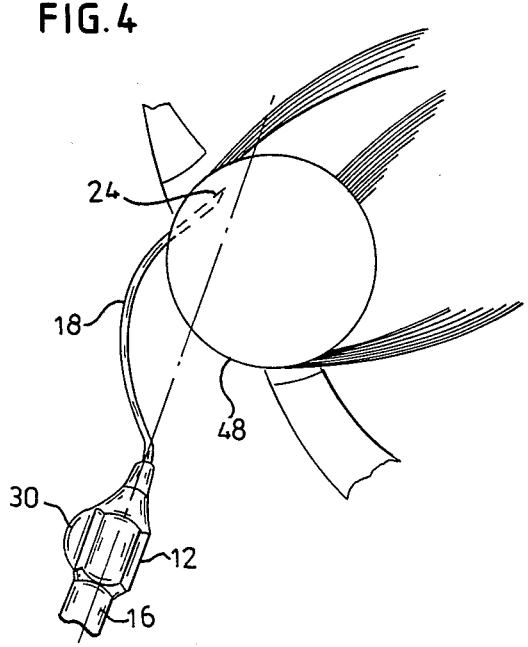
FIG. 4 is a cut-away top view of the ocular area showing the needle of the present invention partially inserted.
Figure 4A:
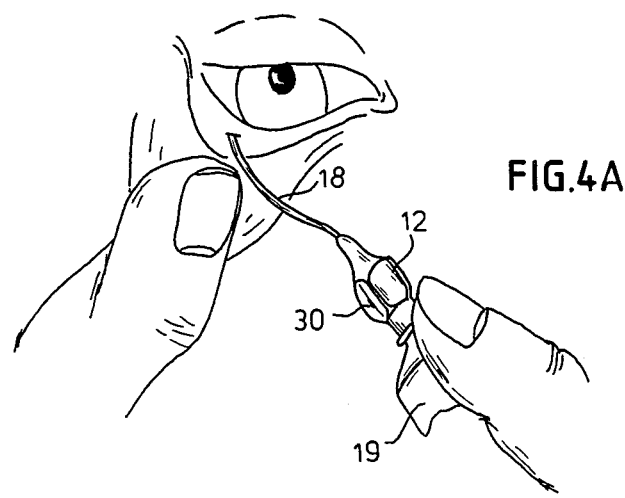
FIG. 4A is an isometric view of FIG. 4 from the surgeon's viewpoint.

In the preferred method, a trans-conjunctival approach is used wherein the lower eyelid is depressed and the straight terminal portion 24 of the needle portion 18 is passed antero-posteriorly in the infero-temporal quadrant of the orbit, so that the tip 26 of the needle 10 is posterior to the equator 29 of the globe 48 (see FIG. 4). The curve of the needle portion 18 is then followed by the syringe for the remainder of the placement, see FIGS. 3 through 5A. Completion of the passage of the needle that is entering into the muscle cone 54 is usually signalled by the surgeon or anesthetist's awareness of having overcome the resistance of the inter-muscular septum. The concave aspect A and the convex aspect B of the needle portion 18 remain approximately within the confines of an axial plane throughout. Of course, the tip may be directed as the surgeon's judgment dictates. The concave aspect A of the needle 18 and therefore the bevel is always nearest the globe of the eye, as can be best seen in FIG. 5.

Figure 2:
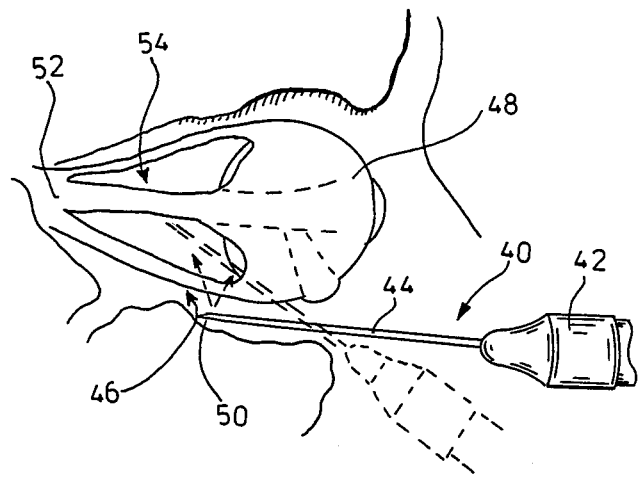
FIG. 2 is a side view of the ocular area showing the insertion of the needle utilized in the prior art.

It is believed that the use of the needle 10 and the method set forth above is advantageous in decreasing many risks inherent in the use of a straight needle for administration of retro-bulbar injections. The use of a straight needle is shown in FIG. 2.

In this prior method, a straight needle, generally noted as 40, is attached to a syringe (not shown), via a hub portion 42. The hollow needle portion 44, of course, extends perfectly straight from the central axis of the hub 42, and upon insertion is first directed straight back in the ocular cavity 46, well away from the eyeball, or globe 48, until the point or tip 50 of the needle 44 is well beyond the globe 48. The needle 44 is then pointed superiorly (see phantom needle) towards the apex 52 of the orbit and inserted to a depth of approximately 2.5 to 3.5 cm, and the injection made into the muscle cone 54. This superior movement of the needle 44, while the needle is within the eye cavity, causes the violation of more intra-orbital tissues and therefore blood vessels, then does the insertion of the needle portion 18 of the present invention. Consequently, the tissue penetrated by the straight needle 44 is stretched as the needle 44 is lifted for passage in the superior direction (towards the top of FIG. 2) with possibility that the shaft of the needle may also displace the globe 48 in the superior direction as the tip is directed towards the apex 52. This further adds to the tension placed on the intra-orbital vessels rendering them more susceptible to rupture.

The curved needle 10 neither stretches the tissues, nor does it displace the globe in order to gain access to the muscle cone 54 behind it, since the curved needle passes around the globe. In the prior art method, the surgeon may displace the globe 48 by digital pressure, to facilitate the passage of the needle 44, a maneuver unnecessary with the use of the curved needle 10 of the present invention.

Another advantage to the use of the method and needle of the present invention is that the use of the curved needle 10 allows an increased distance between the needle portion 18 and the central retinal artery and vein. The curved needle introduced infero-temporally passes more temporal than does the straight needle and is therefore, in relation to these vessels, more remote.

Figure 5:
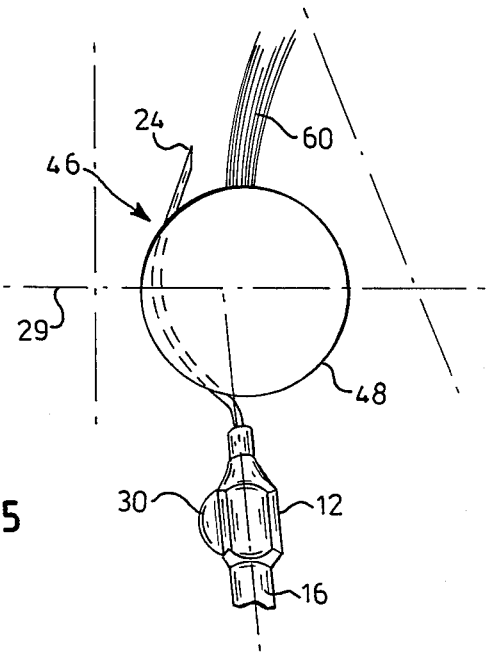
FIG. 5 is a schematic view of the ocular area showing the needle of the present invention fully inserted into the posterior section of the orbit and also showing the optic nerve.
Figure 5A:
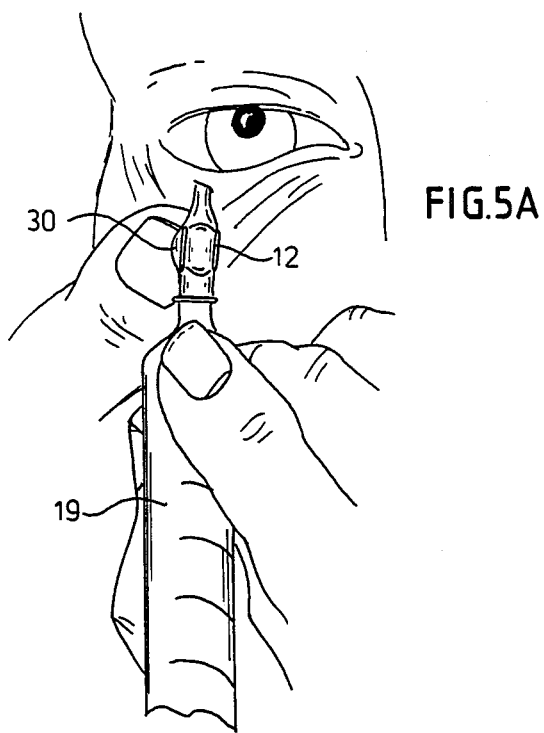
FIG. 5A is an isometric view of FIG. 5 from the surgeon's viewpoint.

As can be seen in FIG. 5, the preferred 25° to 35° angulation of the straight terminal portion 24 of the needle portion 18 approximates the angle at which the optic nerve 60 travels in the axial plane between the globe 48 and the optic foramen. The approach of the needle tip 26 is therefore more parallel to the optic nerve 60 then it would be with the straight needle 44 which passes at a steeper angle superiorly than does the optic nerve.

As can be best seen in FIGS. 4 and 5, using the needle of the present invention with an arc of curvature greater than the arc of curvature of the eye renders penetration of the globe 48 unlikely.

In the preferred embodiment, the arc of curvature of the first and second sections 22, 23 would be the arc of curvature along a sphere having a diameter of 30 mm which would exceed the arc of curvature of almost all eyes.

Figure 6:
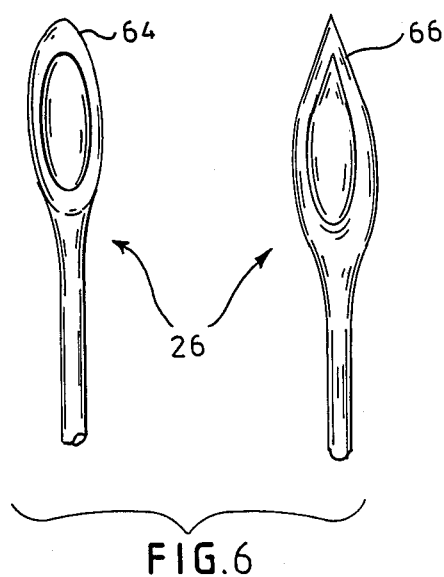
FIG. 6 is a side view of needle tips suitable for use with the needle of the present invention.

The risk described above may be further reduced by using a needle 26, as shown in FIG. 6, which has a bevelled and rounded tip 64 versus the pointed tip of the needle 66.

It is thought that the invention and many of its attendant advantages will be understood from the foregoing description, and it will be apparent that various changes may be made in the form, construction and arrangement of the needle 10, without departing from the spirit and scope of the invention, or sacrifice, all of its material advantages. The form of the invention hereinabove described is merely a preferred or exemplary embodiment thereof.

What is claimed is:

1. A needle for use in the administration of retro-bulbar or peri-bulbar anesthetics, comprising:
   a hub portion having a central longitudinal axis therethrough;
   a generally curved needle portion extending from said hub portion;
   said curved needle portion having a first section extending generally outwardly away from said longitudinal axis of said hub and a second section extending generally inwardly toward said longitudinal axis; and
   a terminal section extending from said second needle section oriented at a predetermined angle in relation to said longitudinal axis.

2. A needle as set forth in claim 1, wherein said hub portion includes means for determining the orientation of said terminal section of said curved needle portion after insertion.

3. A needle as set forth in claim 2, wherein said means for determining the orientation of said terminal section is a vane fixedly attached to said hub on the same plane as said terminal portion.

4. A needle as set forth in claim 1, wherein said terminal section is a generally straight section extending from said second section of said generally curved needle portion.

5. A needle as set forth in claim 1, wherein the tip of said terminal portion is bevelled toward the concave aspect of said generally curved needle portion.

6. A needle as set forth in claim 1, wherein said predetermined angle of said terminal section is thirty degrees.

7. A needle as set forth in claim 1, wherein said hub portion is adapted to mate with a standard syringe.

8. A needle as set forth in claim 1, wherein the arc of curvature of said generally curved needle portion is greater than the arc of curvature of the eye.

9. A method for administering retro-bulbar or peri-bulbar anesthetics which comprises:
- placing a generally curved needle having a hub portion and a straight terminal section on a syringe;
- passing the straight terminal section of the needle antero-posteriorly in the infero-temporal quadrant of the orbit so that the tip of said terminal section is posterior to the equator of the globe;
- following the curve of said needle with the syringe until said terminal portion enters the muscle cone of the eye;
- aspirating with said syringe seeking absence of blood return;
- administering said anesthetics; and
- withdrawing said needle by following the curve thereof.

10. A method as set forth in claim 9, including maintaining the concave and convex aspects of said generally curved needle within the confines of an axial plane.

* * * * *